United States Patent [19]

Chase et al.

[11] Patent Number: 4,920,265

[45] Date of Patent: Apr. 24, 1990

[54] SYSTEM FOR DETERMINING THE BASIS WEIGHT OF CORD REINFORCED TIRE FABRIC

[75] Inventors: Lee M. Chase; John Goss; Philip M. Hegland, all of Cupertino, Calif.

[73] Assignee: Measurex Corporation, Cupertino, Calif.

[21] Appl. No.: 265,314

[22] Filed: Oct. 25, 1988

Related U.S. Application Data

[63] Continuation of Ser. No. 814,384, Dec. 30, 1985, abandoned.

[51] Int. Cl.$^5$ .............................................. G01N 23/06
[52] U.S. Cl. ................................... 250/308; 250/359.1
[58] Field of Search ............... 250/308, 359.1; 378/61, 378/54, 55, 56

[56] References Cited

U.S. PATENT DOCUMENTS

| | | |
|---|---|---|
| 3,497,693 | 2/1970 | Duftschmid et al. . |
| 3,727,054 | 4/1973 | Herrick . |
| 3,757,122 | 9/1973 | Bossen et al. ........................ 250/358 |
| 3,854,046 | 12/1974 | Wood . |
| 3,889,121 | 6/1975 | Bossen ................................. 250/308 |
| 3,914,607 | 10/1975 | Cho et al. ............................. 378/61 |
| 4,389,136 | 6/1983 | Fehrenback ......................... 250/308 |
| 4,706,267 | 11/1987 | Chase et al. . |

FOREIGN PATENT DOCUMENTS

| | | |
|---|---|---|
| 1225396 | 9/1966 | Fed. Rep. of Germany . |
| 2364653 | 6/1975 | Fed. Rep. of Germany ........ 378/61 |
| 2555135 | 6/1976 | Fed. Rep. of Germany . |
| 1312771 | 4/1973 | United Kingdom . |

Primary Examiner—Janice A. Howell
Assistant Examiner—Richard Hanig
Attorney, Agent, or Firm—Spensley Horn Jubas & Lubitz

[57] ABSTRACT

A system for determining the basis weight of cord reinforced tire fabric which involves the use of two radiation source, for example a collimated x-ray beam, and a beta ray source. One of the radiation sources and its corresponding sensor (e.g., the x-ray source) is used to determine the fractional area of the fabric not containing steel cords, while the other (e.g., the beta ray source) is used to measure the average attenuation of radiation passing through the fabric. Both sources and their corresponding sensors are movably mounted on a pair of beams which extend across the width of the fabric web. The source sensor assemblies continuously scan across the fabric width so that information from the entire fabric area is obtained.

20 Claims, 4 Drawing Sheets

SYSTEM FOR DETERMINING THE BASIS WEIGHT OF CORD REINFORCED TIRE FABRIC

This is a continuation of copending application Ser. No. 06/814,384 filed on Dec. 30, 1985 now abandoned.

BACKGROUND OF THE INVENTION

One of the key parameters which must be controlled in the manufacture of cord reinforced tire fabric is its weight per unit area (known as "basis weight"). If basis weight is not determined during the manufacturing process, and adjustments to the process not made to correct deviations from the desired basis weight, large amounts of out of specification material could be made before the process can be corrected. Since steel reinforcement cords are most commonly used in the manufacture of tire fabric, the following specification describes the invention in connection with steel wire reinforced tire fabric. It should be understood, however, that the principles of the invention are applicable to fabric using other types of reinforcing materials.

Continuous determination of basis weight per se is not new. One method which has been used involves measuring the attenuation of radiation such as X-rays or beta radiation as it passes through the material being manufactured. It has long been known that radiation passing through a substance is attenuated in accordance with an exponential function variously known as Beer's Law, Lambert's Law, or Bouguer's Law. As applied to a homogeneous material, a continuous determination of the basis weight can therefore easily be made from a knowledge of the "extinction coefficient" for the material and the attenuation ratio observed when the product is irradiated with an appropriate type of radiation. The "extinction coefficient" is a constant which accounts for both absorption and reflection effects.

Unfortunately, cord reinforced tire fabric is not homogeneous, and basis weight can change due either to changes in the size or spacing of the reinforcing cords, or the thickness of the rubber. This leads to ambiguities in applying the exponential decay equation so that the desired determination cannot be made. To account for the additional variables introduced by the wire cords, it has been suggested that two sources of radiation be used which are absorbed differently by the rubber and the cord. Such a system is described by Bossen in U.S. Pat. No. 3,889,121. The calculations necessary to apply this method, however, are relatively complicated and a number of approximations are required to arrive at a result. A more direct means of determining basis weight is accordingly desirable.

SUMMARY OF THE INVENTION

It is an object of this invention to provide a simple direct system for determining the basis weight of reinforced tire fabric.

The present invention according to a presently preferred embodiment involves the use of two radiation sources to determine the basis weight of steel reinforced tire fabric. One of the radiation sources and its corresponding sensor is used to determine the fractional area of the fabric not containing steel cords, while the other measures the average attenuation of radiation passing through the fabric. Both sources and their corresponding sensors are movably mounted on a pair of beams which extend across the width of the fabric web. The source/sensor assemblies continuously scan across the fabric width so that information from the entire fabric area is obtained.

The source/sensor combination used to determine the area of the fabric not containing steel cords uses a collimated X-ray beam to detect cord edges during the scan. Counting pulses from a constant frequency oscillator between cord edges provides data which allows a calculation of the area of the fabric not including reinforcing cords. At the same time, the second radiation source/sensor is used to ascertain the average attenuation of the fabric.

Since attenuation of radiation is an exponential function of basis weight, the basis weight of the fabric may be calculated using a logarithmic function of the average attenuation, with a correction to account for the presence of the steel cords in the fabric.

DETAILED DESCRIPTION OF THE PREFERRED EMBODIMENT

Figure 1:
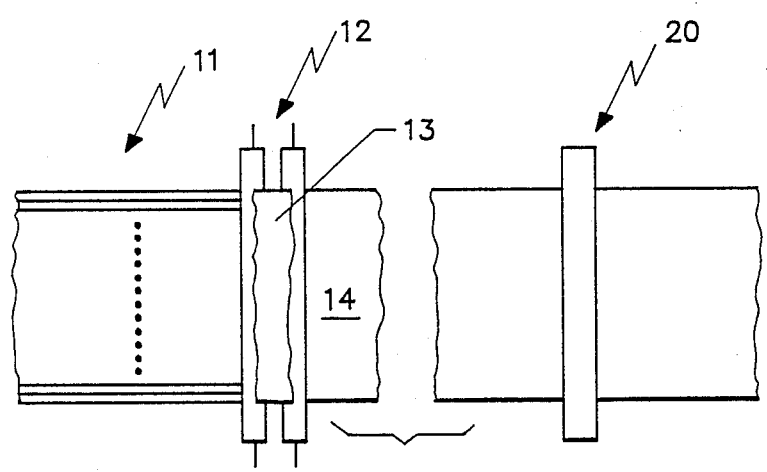
FIG. 1 is a diagramatic plan view of a cord reinforced fabric calender which may be used in connection with the present invention.

FIG. 1 shows a highly diagrammatic plan view of a steel cord tire fabric calender such as may be used in connection with the present invention. Steel cord tire fabric is typically made in widths of about four feet and is usually provided with about 5 to 20 reinforcement cords per inch of width. As shown in FIG. 1, the steel cords 11 enter from the left of the machine and pass under calender rolls 12 which deposit a sheet of latex on top of the travelling cords. The latex pool 13 on top of the rolls 12 is kept replenished by means not shown. A second set of calender rolls (also not shown) are located under the plane of the travelling cords, and apply a similar sheet of latex to the under side of the cords. As the sheets of latex are applied, they flow between the cords and coalesce into a single entity. The fabric 14 leaving the rolls is thus a sheet of latex 15 with a core of spaced steel reinforcing cords 11.

Figure 2:
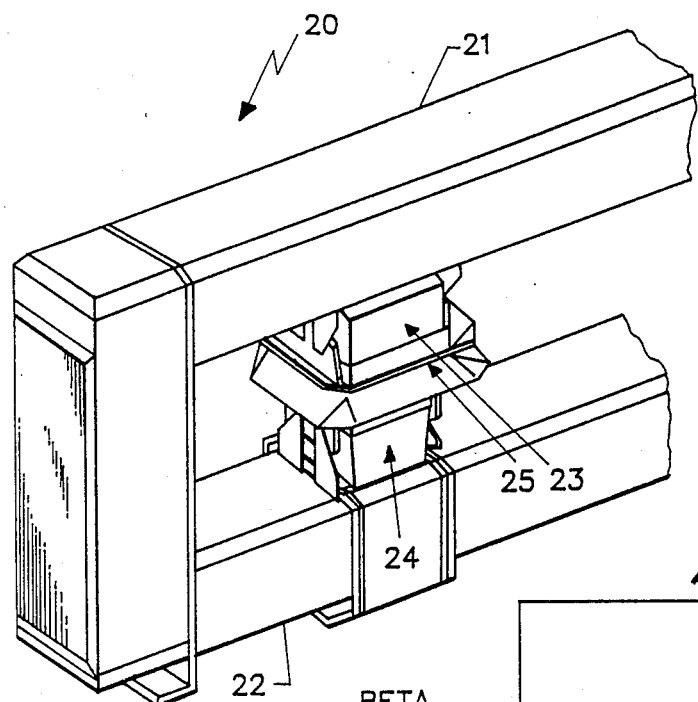
FIG. 2 is a perspective view of a portion of the monitor section of the present invention.

After leaving the calender rolls, and possibly after some further processing, the fabric is passed through a monitor section 20 to determine certain of its characteristics. One such characteristic which may be monitored is the basis weight of the product being manufactured. The monitor section, which holds the sensing portion of the invented apparatus, includes upper and lower traverse beams 21 and 22 as can be seen in FIG. 2. The upper and lower traverse beams are located, as their names imply, over and under the fabric web.

Radiation source/sensor assemblies 23 and 24 are mounted to the upper and lower traverse beams such that they can move back and forth on the beams, with the fabric web passing in the space 25 between them. Means not shown keeps the source/sensor assemblies in alignment, and causes them to scan back and forth across the width of the fabric at a known speed.

Figure 3:
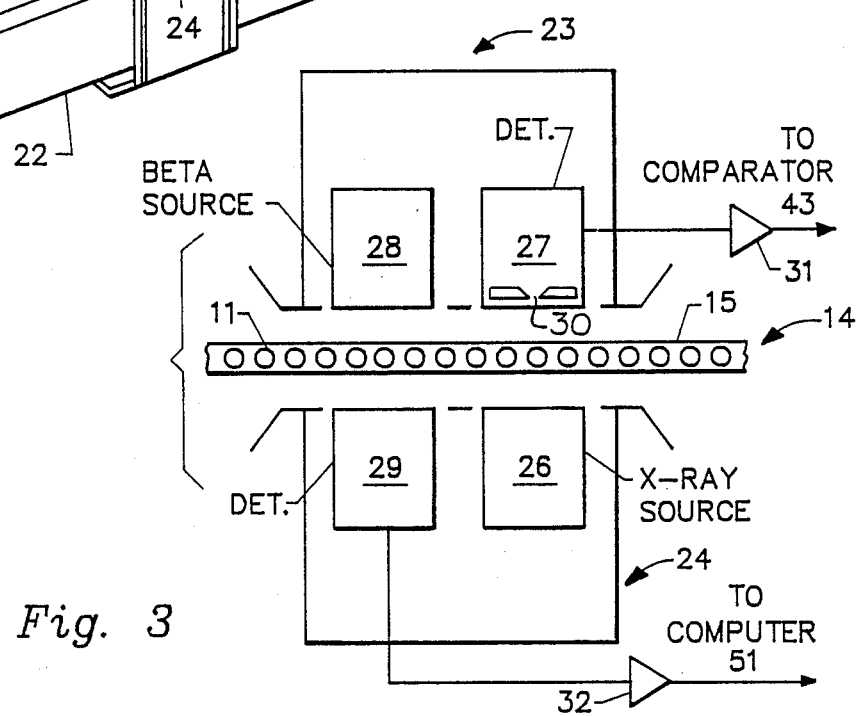
FIG. 3 is a diagramatic cross-sectional view of the radiation sources and sensors of the present invention.

Each of the assemblies 23 and 24 contains a radiation source and a sensor. The sensor in assembly 24 is aligned with the source in assembly 23 and vice versa. As shown in FIG. 3, X-ray source 26 is directed upward through the tire fabric toward sensor 27 and beta source 28 is directed downward toward sensor 29. This opposing arrangement is preferred since it reduces the cross talk between the two systems.

In general terms the beta ray source and sensor is used to measure the average transmission through the fabric in the area irradiated, whereas the X-ray source and sensor are used to correct the readings obtained by the beta source for variations in cord spacing. Consequently, the character of the beams used is different.

A slit 30 is provided in front of X-ray sensor 27. The slit 30 is made narrow so as to admit only a very narrow beam of X-rays to the sensor chamber. A suitable dimension for slit 30 has been found to be 0.010 inch. The sensing area of the beta sensor 29, on the other hand, is not restricted, and the beta radiation passing through a relatively large area of the fabric is sensed by sensor 29. It is preferred that the effective width of the beta ray beam be such that it spans many cords so that the radiation sensed by sensor 29 is representative of the average amount of beta radiation through both the rubber part of the fabric and the part of the fabric containing steel cords. Signals from the X-ray sensor 27 and beta sensor 29 may be amplified by amplifiers 31 and 32, respectively.

Radiation incident on the fabric web 14 from beta source 28 is absorbed and reflected as it passes through the web, and the amount received by sensor 29 is governed by an equation having the following form:

$$I = I_o e^{-kM} \qquad (1)$$

where
- I is the intensity of radiation reaching sensor 29,
- $I_o$ is the intensity of the radiation incident on the fabric,
- e is the base of natural logarithms,
- k is the extinction coefficient of the material, and
- M is the mass part unit area of the fabric.

This equation represents the aforementioned exponential attenuation relationship known as Beer's, Lambert's, or Bouguer's Law.

Since k for rubber and steel are different, and the cord spacing may vary, "k" for the composite material is not a constant so as to allow M to be directly solved for in the equation.

Figure 4:
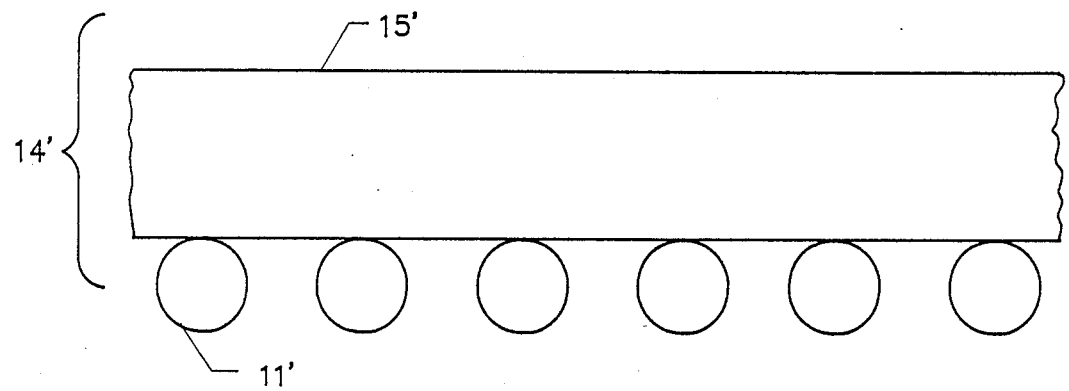
FIG. 4 is a diagramatic cross-sectional view of a hypothetical simplified construction of a cord reinforced fabric.

By making some simplifying assumptions, it is possible to derive an equation for the attenuation which approximates that which is experienced with actual fabric, and which accounts separately for the extinction coefficients of the rubber and the steel. By assuming that the fabric is constructed as shown in FIG. 4, i.e., that as a flat sheet of rubber 15', with the reinforcing cords 11' outside the sheet, the following relationship would hold between the basis weight (mass per unit area) and the attenuation of beta radiation:

$$I = I_o \left[ \frac{W}{S} e^{-krM} + \left(1 - \frac{W}{S}\right) e^{-krM} \times e^{-ksf(d)} \right] \qquad (2)$$

where
- kr is the extinction constant for the rubber,
- ks is the extinction constant for steel,
- M is the basis weight of the rubber,
- f(d) is some function of the diameter of the cords, and
- W/S is the fractional portion of the area of the fabric not covered by steel cord.

Solving for M yields:

$$M = -\frac{1}{kr} \ln \left( \frac{I}{I_o} \times \frac{1}{\left[ \frac{W}{S} + \left(1 - \frac{W}{S}\right) e^{-ksf(d)} \right]} \right) \qquad (3)$$

Where $I/I_o$ is the measured attenuation ratio of fabric as shown in FIG. 4.

Figure 5:
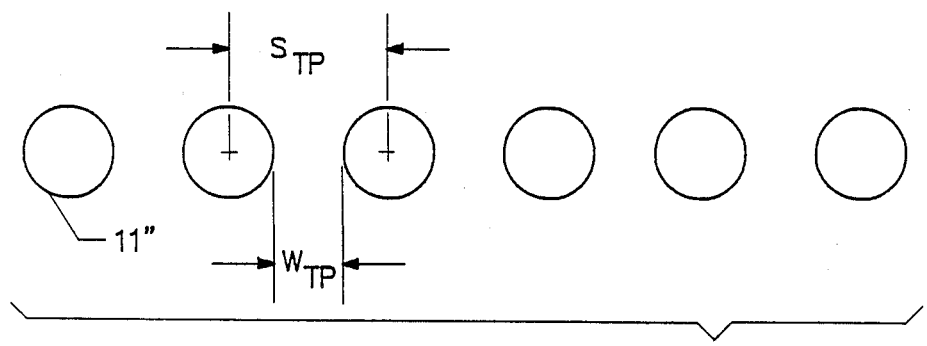
FIG. 5 is a diagramatic cross-sectional view of an arrangement of cords alone without bulk material of the fabric.

The function f(d) could possibly be established by numerical integration, but it is more convenient to determine the value of the entire term $e^{-ksf(d)}$ by experiment. It will be recognized that the term $e^{-ksf(d)}$ defines the fractional amount of radiation which would pass through a single cord of the tire fabric. In order to evaluate this term, a special test piece can be made up of a plurality of spaced steel cords, without any rubber, as illustrated in FIG. 5. By measuring the W/S ratio of this test piece (as described later in this specification) and also the attenuation ratio obtained when the test piece is subjected to the same radiation as used in connection with measuring $I/I_o$ of equation 3, $e^{-ksf(d)}$ can be evaluated.

The equation used is:

$$-ksf(d) = \frac{I_{TP}}{I_{TP_o}} \times \frac{1}{\left(1 - \frac{W_{TP}}{S_{TP}}\right)} \qquad (4)$$

where each of the terms has the same meaning as stated in connection with equations 1 and 2, the subscript TP referring to the test piece.

The basis weight of the postulated rubber sheet with adjacent wire cords as seen by equation (3) is proportional to the natural logarithm of the attenuation ratio times a factor which can be determined. Equation (3) however, slightly overstates the actual basis weight since the actual fabric has the cords within the fabric and hence has less rubber than assumed. An empirical correction factor has been derived to account for this difference. This factor is:

$$J = \left(1 - \frac{A_s}{A_f}\right) \qquad (5)$$

wherein
- J is a correction factor,
- $A_s$ is the nominal cross sectional area of the steel cords, per unit width of the fabric, and
- $A_f$ is the nominal cross sectional area of the fabric per unit width.

While the foregoing equations supply a reasonably accurate relationship between the variables which permits the determination of basis weight, it has been found that to obtain best accuracy, slope and intercept constants should be applied to the foregoing equations. Two empirically determined constants $C_0$ and $C_1$ may be used to establish a final equation (6) as follows:

$$\text{Basis weight} = J\left[C_0 + C_1 \ln\left(\frac{I}{I_0} \times \frac{1}{\left[\frac{W}{S} + \left(1 - \frac{W}{S}\right)e^{-ksf(d)}\right]}\right)\right] \quad (6)$$

where $C_0$ and $C_1$ are empirically determined constants.

The factor W/S may be determined from the known size and spacing of the cords in the fabric, but is preferably determined by actual measurement using the collimated X-ray beam to detect the edges of the cords during a scan, and calculating the actual value of W/S encountered. This method is preferred, since the spacing of the cords may vary somewhat over the width of the fabric. In such case, the average value may not be adequate for determining whether the basis weight is sufficiently constant over the width of the fabric.

Figure 6:
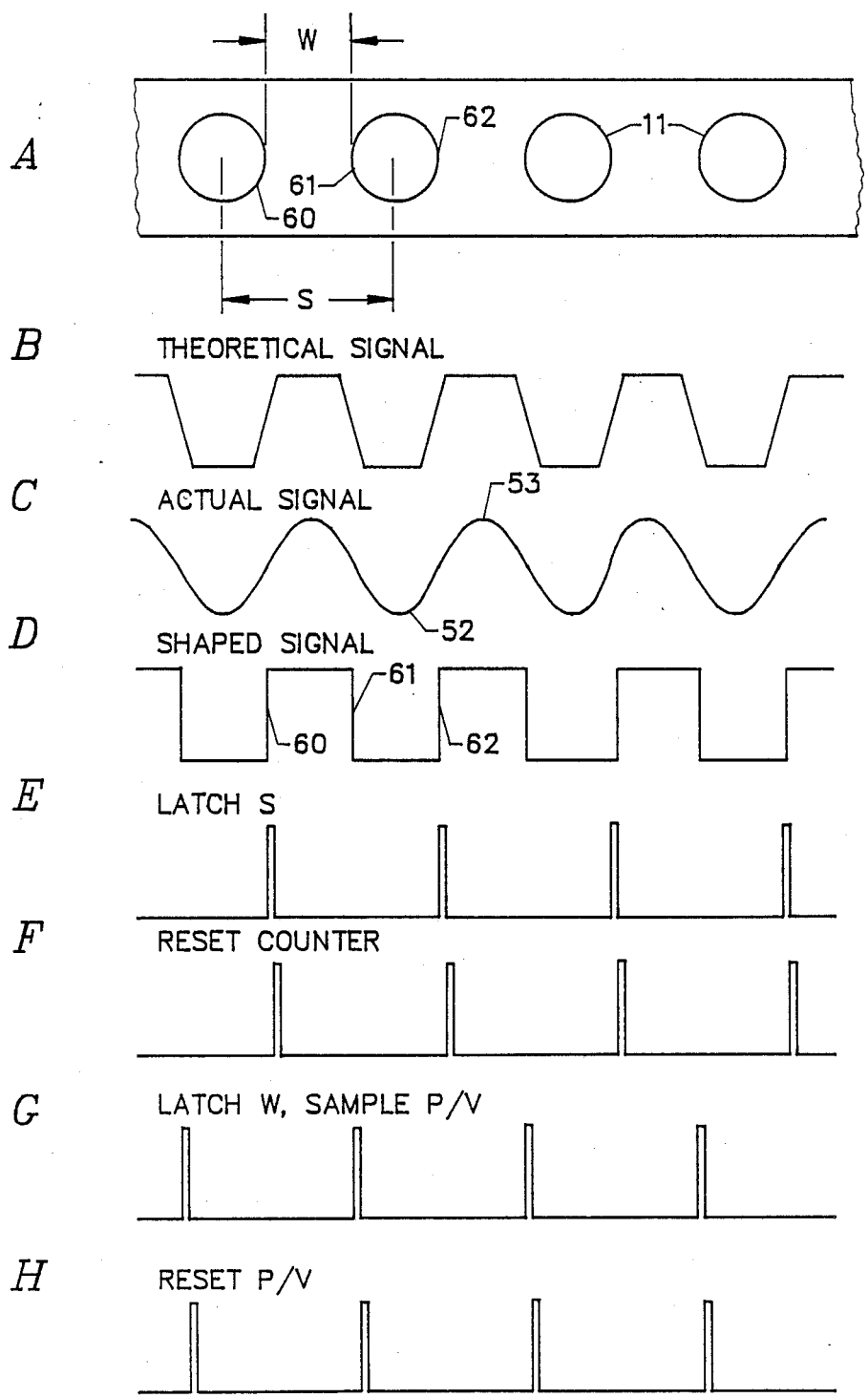
FIG. 6 shows various waveforms representing radiation detection, and the timing of and the relationship between the latching and reset functions.

For purposes of illustration, a small section of tire fabric is shown in FIG. 6 along with waveforms that would be generated by the electronic circuitry of the present invention during a traverse by the sensing elements from left to right. As the X-ray source/sensor 26, 27 traverses the slice of cord illustrated in FIG. 6A, an undulated waveform appears at the output of amplifier 31 (FIG. 3). Ideally, the waveform is trapezoidal as shown in FIG. 6B, but in actual practice the corners are rounded as shown in FIG. 6C. The slope of the leading and trailing edges of the ideal waveform 6B are due to the finite diameter of the collimated X-ray beam, and the rounded corners of actual waveform 6C arise because of non-uniformities in the beam and the partial X-ray transparency of the cords.

Figure 7:
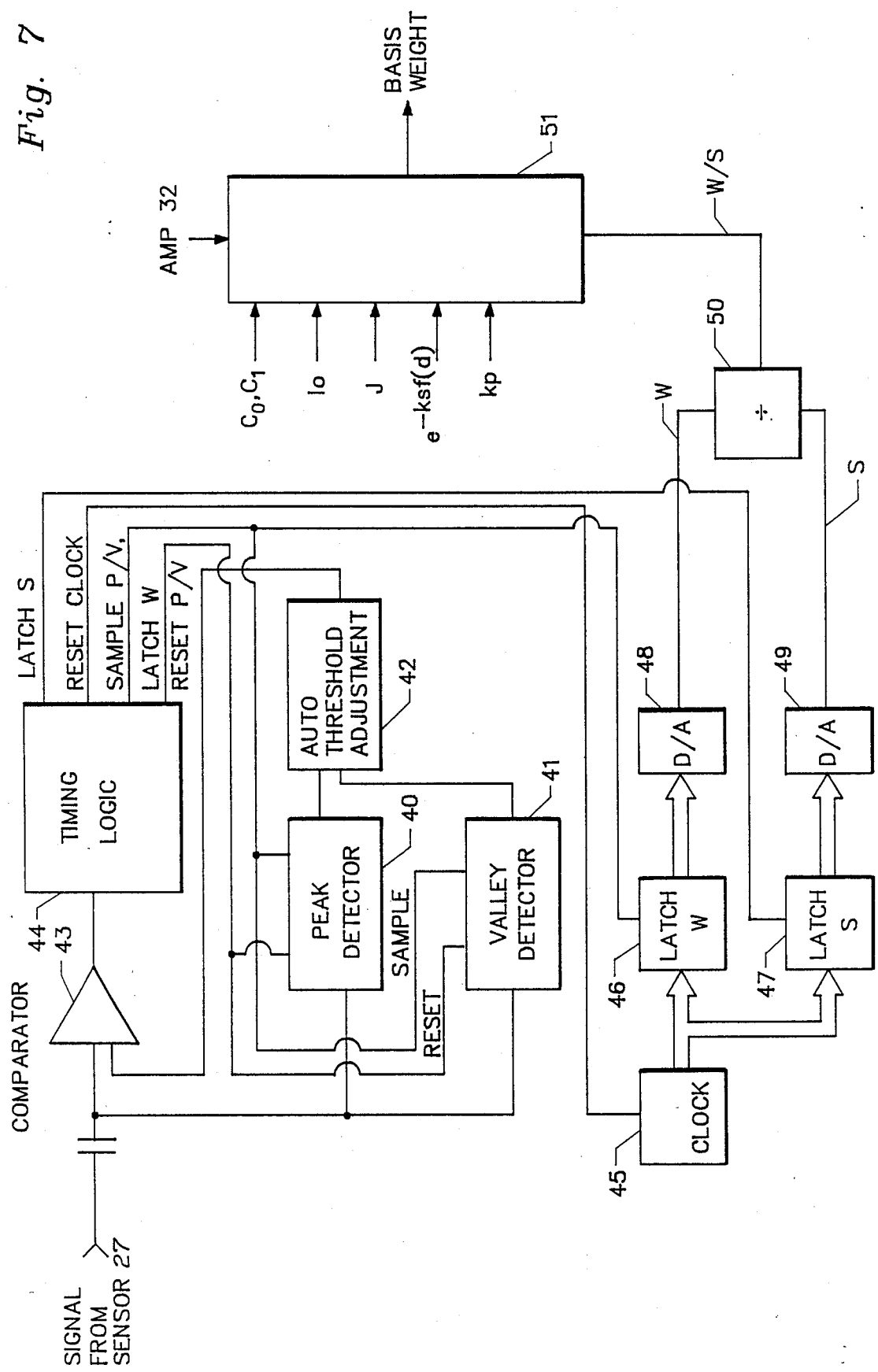
FIG. 7 is a block diagram of the electronic portion of the present invention.

The output of amplifier 31 is fed to peak detector 40 and valley detector 41 (FIG. 7) which hold the maximum and minimum voltages 53 and 52 experienced, respectively, until reset. The maximum and minimum voltages held by the peak and valley detectors are fed to the automatic reference circuit 42 whenever the detectors (40, 41) receive a "sample" pulse from the timing logic module 44. In response to an input from the peak and valley detectors, the automatic reference circuit 42 generates a voltage approximately equal to one-half the peak plus valley voltage and couples this voltage to comparator 43 to act as a reference voltage for the comparator. Ideally, the reference voltage is equal to one half the peak plus valley voltage, but since the actual waveform of FIG. 6C may not be perfectly symmetrical, the required reference voltage may not be exactly the ideal voltage. The reference voltage is held until another sample pulse causes the voltage to change. The output of comparator 43 is the shaped signal of waveform 6D. It goes negative when the X-ray source/sensor passes the leading edge of a cord and positive at a trailing edge. The reference voltage may have to be adjusted slightly so that the transitions in the waveform of FIG. 6D occur when the X-ray beam is centered over a cord edge.

Timing logic module 44 is driven by comparator 43 and provides timing signals as shown in FIG. 6. As can be seen from the signals of FIG. 6F, the counter 45 is reset each time the X-ray beam leaves a cord and starts to traverse a space (shown, e.g., at 60 of FIG. 6). The counter 45 counts cycles of an internal fixed frequency oscillator. The frequency of the oscillator can, if desired, be correlated with the scan speed of the X-ray source/sensor so that the count in counter 45 will be numerically equal to the distance travelled by the source/sensor in whatever units of distance is convenient. When the space starting at 60 has been traversed and the X-ray beam is starting to traverse a cord (61), the count in counter 45, which is then representative of the width of the space (W in FIG. 6A), is latched into latch 46. At the same time, a sample pulse is sent to the peak and valley detectors 40, 41. Immediately following the sample pulse, the peak and valley detectors are reset so as to be in condition to detect the maximum and minimum voltage generated during the next cycle, i.e., voltages 52 and 53 of FIG. 6.

The next cord edge detected (62) causes the count in counter 45, which at this time is proportional to the cord spacing (S in FIG. 6A), to be latched into latch 47. This is immediately followed by resetting of the counter for another cycle.

It may be noted that the reset pulses (FIGS. 6F and 6H) are shown on the timing diagram as apparently occurring at the same time as the latching pulses (FIGS. 6E and 6G). In actuality, the reset pulses occur slightly later in time so as not to interfere with the latching and sampling functions.

The counts in latches 46 and 47 are fed to D/A converters 48 and 49, the outputs of which are electrical signals proportional to the open space between cords (W) and the cord spacing (S) respectively. Divider 50 provides the normalized open space signal (W/S).

The output of divider 50 (W/S) is coupled to computer 51, as is the output of beta sensor 29 after it has been amplified by amplifier 32 (FIG. 3). The various other factors which are needed to evaluate equation (6) are entered into computer 51 prior to the start of the measurement process. The factor $I_0$ is determined by a measurement of the output of beta sensor 29 when no fabric is in the space 25, $e^{-ksf(d)}$ is determined by measuring the output of beta sensor 29 when a layer of spaced cords (as illustrated in FIG. 5) is inserted into space 25, and kr is determined by measuring the output of beta sensor 29 when a standardized sheet of rubber is inserted into space 25. The factors J, $C_0$ and $C_1$ are determined from empirical testing and are manually loaded in the computer.

When the various constants are loaded into the computer, the computer 51 evaluates equation (6) on an on line basis and provides an output which is representative of the basis weight. As the source/sensor assemblies 23, 24 scan across the width of the fabric and the fabric passes through the monitor section 20, the basis weight of the fabric, as well as its variation from side to side are continuously measured. The output of computer 51 can be coupled to a visual readout means, if desired, or to a control mechanism for automatic control of the calender process, or both.

What has been described is a novel system for measuring the basis weight of steel cord reinforced tire fabric. Those skilled in the art will readily preceive how to modify the presently preferred embodiment of the invention disclosed herein and hence the following claims should be construed to cover all equivalent structures which fall within the true scope and spirit of the invention.

We claim:

1. A system for determining the weight per unit area of a sheet of material having a core comprised of spaced cords which comprises:
   (a) a radiation source for irradiating an area of said sheet with radiation;
   (b) first means for generating a first signal dependent on the fraction of the radiation from said radiation source which passes through said sheet;
   (c) second means for providing a second signal representative of the fractional area of the material between the cords; and
   (d) third means for altering said first signal by an amount dependent on the second signal.

2. A system as recited in claim 1 and further including means for generating a third signal dependent on the logarithm of said altered first signal.

3. A system as recited in claim 2 and further including means for altering said third signal dependent on the ratio of the cross sectional area of said sheet per unit width to the cross sectional area of said cords per unit width.

4. A system as recited in claims 1, 2 or 3 where said radiation source is a source of beta rays.

5. A system for determining the weight per unit area of cord reinforced fabric having spaced cords which comprises:
   (a) a source of radiation for irradiating an area of fabric being tested;
   (b) a detector for generating a first signal representative of the amount of said radiation passing through said fabric;
   (c) means for providing information representative of the locations of cord edges and for generating a second signal, dependent on the cord edge locations, indicative of the fractional area between the cords;
   (d) means for altering the magnitude of said first signal by an amount dependent on the magnitude of said second signal; and
   (e) means for providing a third signal dependent on the logarithm of the magnitude of said altered first signal.

6. A system for determining the weight per unit area of cord reinforced fabric having spaced cords which comprises:
   (a) a first radiation source for irradiating an area of said fabric with radiation;
   (b) means for generating a first signal dependent on the fraction of said first radiation passing through said fabric;
   (c) a second radiation source for irradiating said fabric;
   (d) detection means for detecting a narrow portion of the radiation from said second source passing through said fabric, the narrow portion is small compared to the size of said cords;
   (e) means responsive to said detection means for generating a second signal dependent on whether a cord is between said detection means and said second radiation source;
   (f) means for causing said second radiation source and said detection means to move with a predetermined velocity across said fabric in a direction substantially normal to the direction of said cords;
   (g) means for generating a third signal responsive to said second signal dependent on the fractional distance across said fabric not occupied by said cords; and
   (h) means for altering said first signal dependent on said third signal.

7. A system according to claim 1 wherein the means for providing a second signal representative of the fractional area of the material between the cords includes means for measuring distance between adjacent edges of the cords of the fabric.

8. A system according to claim 7 wherein the means for measuring the distance between cord edges includes means for detecting cord edge locations and means for determining distance between cords in accordance with the detected cord edge locations.

9. A system according to claim 5 further comprising means for altering said third signal by an amount dependent on the ratio of the cross-sectional area of said fabric per unit width to the cross-sectional area of said cords per unit width.

10. A system according to claim 6 further comprising means for altering said altered first signal by an amount dependent on the ratio of the cross-sectional area of said fabric per unit width to the cross-sectional area of said cods per unit width.

11. A method of determining the weight per unit area of a cord reinforced fabric comprising the steps of:
   (a) irradiating an area of the fabric with radiation;
   (b) detecting the amount of radiation passing through the fabric;
   (c) determining the fractional area of the fabric not occupied by cords; and
   (d) determining the weight per unit area of the fabric based on the detected radiation and the determined fractional area.

12. A method according to claim 11 further comprising the step of correcting the determined weight per unit area of the fabric by an amount dependent on the ratio of the cross-sectional area of the fabric per unit width to the cross-sectional area of the cords per unit width.

13. A method according to claim 11 wherein the step of determining fractional area includes determining the distance W between adjacent cord edges and the spacing S of the cords and wherein the step of determining the weight per unit area of the fabric includes solving an equation having the ratio W/S as a variable.

14. A device for determining the weight per unit area of cord reinforced fabric, comprising:
   (a) a first radiation sensor including a first radiation source for irradiating a relatively wide area of the fabric with a first type of radiation and a first detector opposite the first radiation source for detecting the intensity of the first type of radiation transmitted through the sheet over a relatively wide area of the fabric, and for generating a first signal indicative of the detected intensity of the first type of radiation;
   (b) a second collimated radiation sensor including a second radiation source for irradiating the fabric with a second type of radiation and a second detector opposite the second radiation source for detecting the second type of radiation transmitted through the sheet at an area of the sheet narrower than the wide area, and for generating a second signal, based upon the detected second type of radiation, indicative of the cord edge locations; and (c) means operatively coupled to the first and second sensors for receiving the first and second signals and determining the weight per unit area of the fabric based upon the first and second signals.

15. The device of claim 14, further including a scanner for scanning the sensors back and forth along a line.

16. The device of claim 14, wherein the means operatively coupled to the first and second sensors is made to determine, from the second signal, the spacing between cord edges and, based upon the determined cord edge spacings, to further determine the fractional area of the fabric not containing cords and to compute the weight per unit area of the fabric from the determined fractional area and the first signal.

17. A system for determining the weight per unit area of a cord reinforced fabric, comprising:
   (a) a fabric including spaced reinforcing cords;
   (b) a first radiation sensor including a first radiation source for irradiating a relatively wide area of the fabric with a first type of radiation and a first detector opposite the first radiation source for detecting the intensity of the first type of radiation transmitted through the sheet over a relatively wide area of the fabric, and for generating a first signal indicative of the detected intensity of the first type of radiation;
   (c) a second collimated radiation sensor including a second radiation source for irradiating the fabric with a second type of radiation and a second detector opposite the second radiation source for detecting the second type of radiation transmitted through the sheet at an area of the sheet narrower than the wide area, and for generating a second signal, based upon the detected second type of radiation, indicative of the cord edge locations; and
   means operatively coupled to the first and second sensors for receiving the first and second signals and determining the weight per unit area of the fabric based upon the first and second signals.

18. The system of claim 17, further comprising scanning means for scanning the sensors back and forth across the fabric along a line perpendicular to the longitudinal direction of the cords.

19. The system of claim 18, wherein the means operatively coupled to the first and second sensors is made to determine the spacing between corresponding edges of adjacent cords and the spacing between adjacent edges of adjacent cords based upon the second signal and to compute the weight per unit area of the cord reinforced fabric from the determined spacings and the first signal.

20. A device for determining the weight per unit are of a sheet of material having a core including spaced cords, the device comprising:
   a radiation source for irradiating an area of the sheet;
   means for generating a first signal dependent on the radiation from the radiation source transmitted through the sheet; and
   computer means operatively coupled to the means for generating a first signal, said computer means determining the weight per unit area of sheet material based upon the first signal and the fractional area of the material not occupied by the cords.

* * * * *